United States Patent
Alden

(10) Patent No.: US 6,743,249 B1
(45) Date of Patent: Jun. 1, 2004

(54) TREATMENT DEVICE FOR PHOTODYNAMIC THERAPY AND METHOD FOR MAKING SAME

(76) Inventor: Philip G. Alden, 259 Chemung St. #3, Corning, NY (US) 14830

( * ) Notice: Subject to any disclaimer, the term of this patent is extended or adjusted under 35 U.S.C. 154(b) by 0 days.

(21) Appl. No.: 09/513,573

(22) Filed: Feb. 25, 2000

(51) Int. Cl.[7] .............................................. A61N 5/006
(52) U.S. Cl. ........................................... 607/88; 606/1
(58) Field of Search ............................ 607/88–90, 92; 606/1, 2, 3, 9, 10, 11–16

(56) References Cited

U.S. PATENT DOCUMENTS

| | | | | |
|---|---|---|---|---|
| 4,761,047 A | * | 8/1988 | Mori ............................ | 607/88 |
| 4,852,549 A | * | 8/1989 | Mori ............................ | 607/92 |
| 5,054,488 A | | 10/1991 | Muz ............................ | 128/633 |
| 5,278,432 A | * | 1/1994 | Ignatius et al. ............... | 257/88 |
| 5,616,140 A | | 4/1997 | Prescott ....................... | 606/10 |
| 5,660,461 A | * | 8/1997 | Ignatius et al. ............... | 362/241 |
| 5,766,234 A | | 6/1998 | Chen ............................ | 607/92 |
| 5,830,136 A | | 11/1998 | Delonzor et al. ............. | 600/323 |
| 5,944,748 A | * | 8/1999 | Mager et al. ................. | 607/88 |
| 5,957,960 A | * | 9/1999 | Chen et al. ................... | 607/92 |
| 6,048,359 A | * | 4/2000 | Biel ............................. | 607/92 |

FOREIGN PATENT DOCUMENTS

| | | | | |
|---|---|---|---|---|
| WO | WO98/44852 | 10/1998 | ......... | A61B/17/132 |

* cited by examiner

*Primary Examiner*—Roy D. Gibson
*Assistant Examiner*—Peter J Vrettakos
(74) *Attorney, Agent, or Firm*—Philip G. Alden

(57) ABSTRACT

A light-emitting treatment device including one or more light-emitting elements disposed in a flexible and stretchable pad (or a body-conforming shaped article) defining a skin- or tissue-adhering surface having an inherently tacky characteristic for secure application to the skin, tissue, or other external or internal regions of the patient's body. The light-emitting treatment device is configured to contact and adhere to the skin or tissue of a patient, and irradiate an underlying region for photodynamic therapy. The treatment device may be fabricated from a shell member and a filler material (such as a molded silicone rubber shell member and a silicone gel filler material), to provide a skin-adhering, peelable, washable, and repositionable contact surface.

20 Claims, 2 Drawing Sheets

TREATMENT DEVICE FOR PHOTODYNAMIC THERAPY AND METHOD FOR MAKING SAME

BACKGROUND OF THE INVENTION

1. Field of the Invention

This invention relates generally to medical devices for topical photodynamic therapy (PDT) treatment of patients, and particularly to a flexible and conforming pad or a shaped-article containing light-emitting elements which is placed in contact with the patient's skin or tissue, and a method for making that apparatus.

2. Technical Background

The field of topical photodynamic therapy (PDT) and medical devices for practicing photodynamic therapy are known. In one approach, various types of pads, patches, or garments containing light-emitting elements (or having light-emitting elements attached thereto) are placed in contact with the skin or other tissue of the patient to irradiate that portion of the skin or tissue with light. The light may itself provide a therapeutic benefit due to its characteristic wavelengths, or may act in combination with a pharmacological agent (which is applied topically to the patient's skin or tissue, or is injected or ingested by the patient) which reacts with the light and produces a therapeutic benefit. The pharmacological agent may accumulate in the region being treated, or may react upon exposure to the light at the exposed region while traversing within the circulatory system.

Representative examples of pads, patches, garments, or shaped objects which contain or carry light-emitting elements for use in photodynamic therapy are known.

One approach is to provide a flexible "circuit board" containing an array or network of diode lasers or LEDs bonded to a silicon pad and encased by a clear, co-molded silicone cover which serves as a lens for the light-emitting elements. One specific type of light-emitting element proposed for the array is a vertical-cavity surface-emitting laser (VCSEL) that is wavelength-specific for PDT or immunotherapy. Such an array of light-emitting elements within the silicon cover may be shaped to conform to certain regions of the patient's body, such as a glove or sock for the patient's hand or foot, a band which may be wrapped around an extremity such as an arm or leg, garments which may cover a large portion of the patient's torso or trunk, as well as strips or patches designed to access substantially remote or partially-internal areas such as the gums within the patient's mouth. In some applications, the pads may be adhered to the patient's skin or other tissue using an adhesive.

Other approaches permit internal or more invasive uses of flexible light-emitting pads or patches for photodynamic therapy via conventional surgery or laparoscopy, with representative examples of treatment sites being a region of the pericardium or heart muscle, around or within an artery or arterial stenosis, or adjacent to or within an organ or tumor.

SUMMARY OF THE INVENTION

The invention is a photodynamic therapy (PDT) treatment device for delivering light from one or more light-emitting elements which is flexible or sufficiently pliable to conform to the skin or tissue of the patient, and which provides a skin-adhering surface which adheres directly to the patient's skin or tissue upon contact, will automatically peel from the skin (or itself) if wrapped or stretched too tightly, and may be selectively removed, washed, and repositioned as desired.

In one embodiment, the light-emitting treatment device is a flexible, surface-conforming pad or covering including a flexible polymeric shell having an area to receive the light-emitting elements, the shell being at least partially filled or covered with a flexible filler or liner material such as a cured gel which retains a skin-adhering quality after curing, with the shell and liner material providing an exposed skin-adhering surface positioned generally between the light-emitting elements and the patient's skin. In an alternate embodiment, the light-emitting treatment device is similarly fashioned as a generally rigid yet sufficiently pliable surface-conforming shaped-article.

The invention further includes a method for making the light-emitting treatment device having a skin-adhering surface which enhances manufacturability by permitting multiple light-emitting elements and circuitry to be laid out without subsequent disturbance, embedded at or slightly above room temperature without being subjected to a molding process, substantially surrounded and secured to maintain alignment and maximize heat dissipation, and providing more uniform and reproducible light transmission or diffusion properties compared with the slippage, gaps, and irregularities that may could occur when layering the light-emitting elements between pre-molded silicone sheets as taught in the prior art.

In one embodiment, the method includes providing a molded polymeric or flexible polymeric shell member defining an area for receiving the light-emitting elements, positioning the light-emitting elements on or within the shell member, at least partially filling the shell member or partially covering the light-emitting elements with a gel liner material in a viscous liquid state, and curing the liner material to provide a flexible pad or shaped-article which maintains a skin-adhering surface which may be applied to a region of the patient's skin or tissue such that the light-emitting elements irradiate that region.

In summary, the invention relates to a light-emitting medical treatment device including a shell member and a liner (or filler) material defining a surface which is skin-adhering. The shell member, liner material, and light-emitting elements form an assembly configured to emit energy for photodynamic therapy onto a body surface. The treatment device may be either substantially flexible or sufficiently rigid to hold a predetermined shape (yet sufficiently pliable so as to be applied to the patient's body), and may be fabricated to conform to any selected body surface or to a predetermined body shape. The shell member and liner material may be made of compatible polymeric materials, such as a molded silicone rubber shell member and silicone gel liner material. The shell member and liner material may be configured in a substantially integral and unitary structure, and may form a light-diffusing and heat-dissipating covering for the light-emitting elements. The light-emitting elements may be laser diodes, LEDs, optical fibers, or any other suitable source of therapeutic light.

The invention also relates to a product made from the process or method of this invention.

Still other representative embodiments and advantages of the present invention and methods of construction of the same will become readily apparent to those skilled in the art from the following detailed description, wherein only the preferred embodiments are shown and described, simply by way of illustration of the best mode contemplated for carrying out the invention. As will be realized, the invention is capable of other and different embodiments and methods of construction, and its several details are capable of modification or adaptation in various respects all without departing from the invention as disclosed and claimed. Accordingly, the appended drawings and description contained herein, as well as the descriptions and drawings contained in the applications and associated documents to which the benefit of priority has been claimed and which are incorporated herein by reference as though fully set forth, are to be regarded as illustrative in nature and not as restrictive or limiting.

BRIEF DESCRIPTIONS OF THE DRAWINGS

Figure 10:
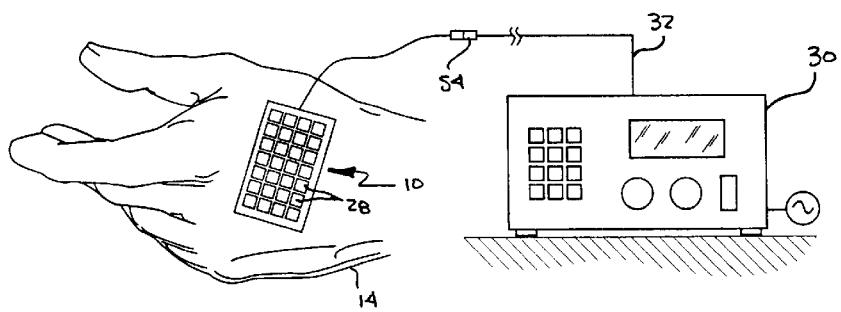
Figure 11:
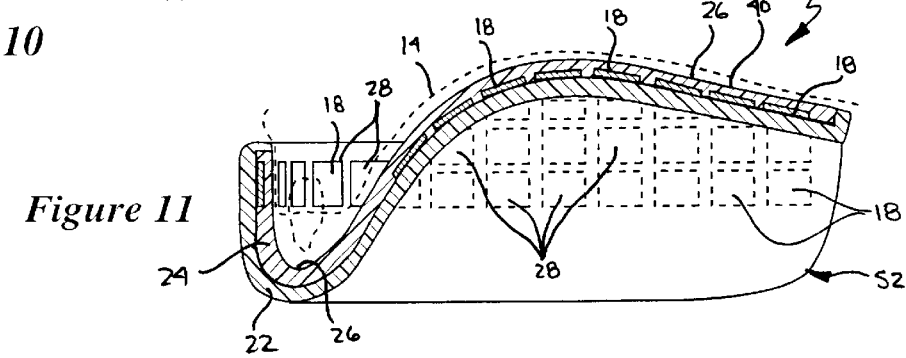

FIG. 10 is a perspective diagrammatic view of a flexible pad-type embodiment of the light-emitting treatment device of the present invention disposed on a region of a patient's body, the light-emitting treatment device being operatively connected to a control unit and power supply; and FIG. 11 is a side cross section diagrammatic view of a shaped-article type embodiment of the light-emitting treatment device of the present invention, the representative example of the shaped-article embodiment being a dental mouthpiece including VCSELs as light-emitting elements positioned in confronting relationship to the gums or the palate of the patient (shown in phantom).

DETAILED DESCRIPTION OF THE PREFERRED EMBODIMENTS

Various preferred embodiments of the light-emitting treatment device of the present invention are described below and shown in FIGS. 1–11, with the light-emitting treatment device being generally referenced herein by the numeral 10.

Referring to FIGS. 1–4, one embodiment of the light-emitting treatment device 10 is configured as a pad 12 or patch which is flexible and conforms to a selected region of a patient's body 14, or referring to FIG. 11 is a shaped-articled 16 configured to conform to a predetermined shape of the corresponding portion of the patient's body 14.

The light-emitting treatment device 10 is particularly adapted to be placed in confronting contact with the patient's body 14 and irradiate a region of the skin, tissue, or other external, exposed, or internal organs of the patient's body 14, and used to provide topical or surface photodynamic therapy (PDT) to that region or surface, including PDT which requires applying generally uniform intensity light energy for long periods. Hereafter, the terms "skin" and "tissue" will be used interchangeably or alternately, and the external skin, external organs, exposed internal tissue surfaces, and internal tissue or organs may be referred to collectively and interchangeably as "skin" or "tissue." The term "tissue" is further understood to broadly encompass the skin or any other body surfaces to which the light-emitting treatment device 10 would be applied on or within a patient, including exposed or externally-accessible regions of the patient's body 14, or regions of the patient's body 14 requiring an invasive procedure such as open surgery or laparoscopy to access.

Figure 1:
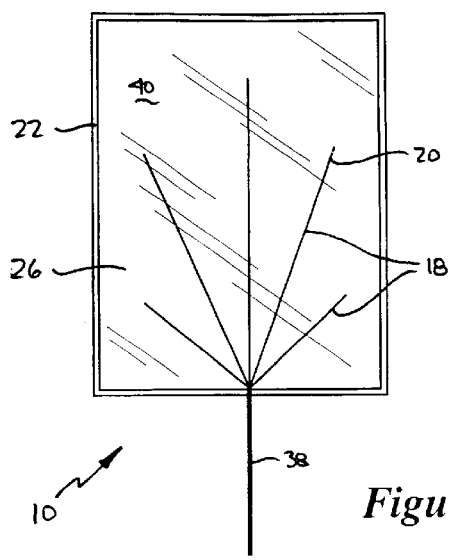
FIG. 1 is a plan view of one embodiment of the light-emitting treatment device of the present invention showing a plurality of radially diverging optical fibers as the light-emitting elements.
Figure 2:
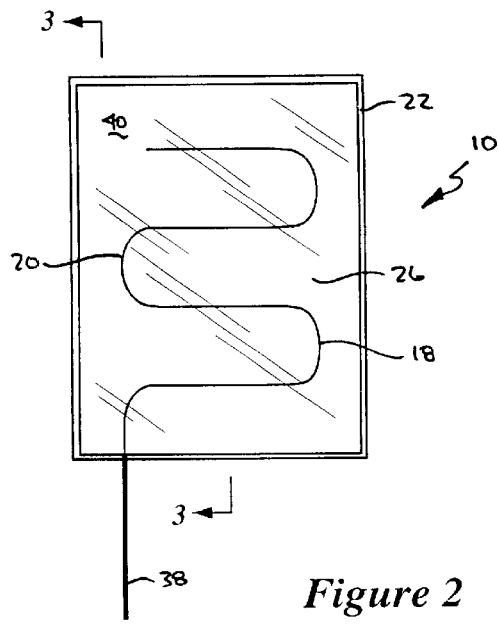
FIG. 2 is a plan view of view of another embodiment of the light-emitting treatment device of the present invention showing a serpentine optical fiber as the light-emitting element.

Referencing particularly to FIGS. 1 and 2, embodiments of the light-emitting treatment device 10 are shown having light-emitting elements 18 in the form of a plurality of radially-diverging optical fibers 20 or one or more serpentine optical fiber 20.

Figure 3:
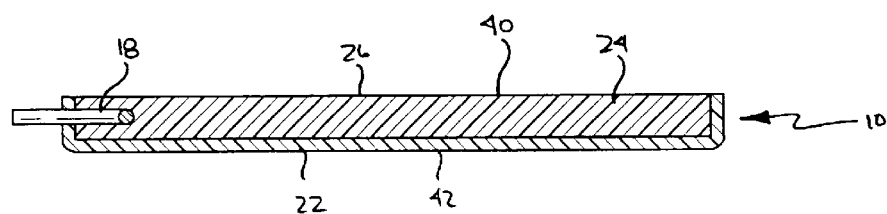
FIG. 3 is a cross-section of the light-emitting treatment device of the present invention taken through line 3—3 of FIG. 2, the light-emitting treatment device being constructed of a shell member, a liner or filler material, and a light-emitting element embedded in the liner material.

FIG. 3 illustrates a cross-sectional view of the light-emitting treatment device 10 of FIG. 2 constructed of a shell member 22 defining a recessed area to receive the light-emitting elements 18, a filler or liner material 24 formed or filled into the recessed area of the shell 22, and an optical fiber 20 embedded therein as the light-emitting element 18. The shell member 22 and the liner material 24 provide an exposed surface 26 on the skin-facing or tissue-confronting side of the light-emitting treatment device 10 at which the liner material 24 may contact the skin or other tissue of the patient's body 14.

Figure 4:
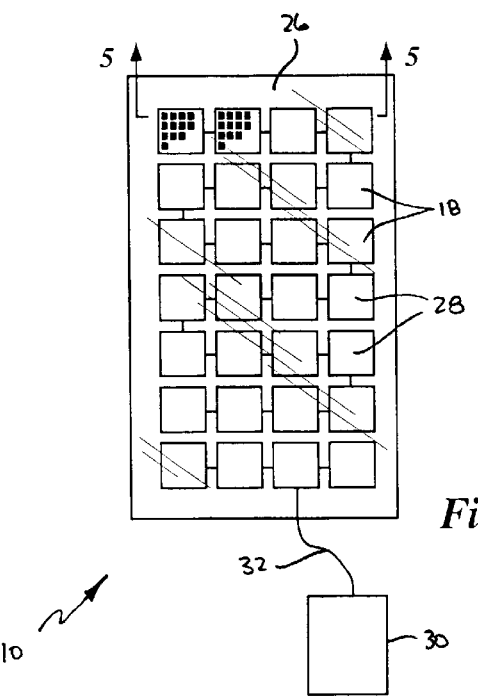
FIG. 4 is a plan view of an alternate embodiment of the light-emitting treatment device of the present invention similarly constructed of a shell member, a liner material, and a plurality of vertical cavity surface-emitting lasers (VCSELs) arranged in an array, at least partially embedded in the Liner material, and operatively coupled to an independent control and power supply.

FIG. 4 illustrates an embodiment of the light-emitting treatment device 10 in which a plurality of light-emitting elements 18 are each made of one or more vertical cavity surface-emitting lasers (VCSELs) 28-or chips containing one or a plurality of such VCSELs 28—arrayed in a pattern or configuration as desired and operatively coupled to an independent control unit and power supply 30 using any suitable wire or cable 32. A plurality of the VCSELs 28 or light-emitting diodes (LEDs) are disposed in the desired array or pattern, and may be adhered to or mounted on or within the shell member 22 or other substrate to form a light-emitting treatment device 10. The array of VCSELs 28 or LEDs may be wired in series, parallel, or combinations of series and parallel using suitable patterns among adjacent rows or via a peripheral scheme.

Together, the shell member 22 and liner material 24 define the shape and consistency of the light-emitting treatment device 10, and may form an integral or unitary structure which will not separate from one another when flexed or stretched sufficiently for application to the intended region of the patient's body 14.

One suitable material for the shell member 22 and liner material 24 is a silicone into which one or more light-emitting elements 18 may be partially or completely embedded. The silicone or other material may be used to diffuse the light transmitted from the light-emitting elements 18 generally uniformly over a region of the patient's body 14 being irradiated.

The shell member 22 is preferably made of a molded and cured liquid silicone rubber material such as dimethylsilicone which is sufficiently rigid to support and retain the liner material 24. The shell member 22 is preferably made of a highly flexible, compressible, and deformable material having a durometer rating of approximately 20A (Shore units) or less, a tensile strength of about 450 psi minimum, elongation of about 650% minimum, and a tear strength of about 70 ppi minimum. One suitable material is LSR-10 liquid silicone rubber available under Product Identification No. 40023 from Applied Silicone Corporation of Ventura, Calif.

The liner material 24 is preferably made of a generally high-strength and firm silicone gel composition which is inherently tacky to silicone rubber or skin. The liner material 24 has a peel strength of approximately 0.5 ppi (lb./in.) or less from a stainless steel surface, thus permitting the light-emitting treatment device 10 to automatically peel away from the skin of the patient if high lateral forces are applied, such as if the light-emitting treatment device 10 were stretched or wrapped too tightly around or across the region of the patient's body 14 being treated. The liner material is hydrophobic, and may be cleaned in water and reused without a substantial reduction in its intrinsic tackiness. One suitable material is a silicone gel material that is available under Product Identification No. 40022 from Applied Silicone Corporation of Ventura, Calif.

Both the shell member 22 and liner material 24 generally appear substantially indistinguishable to the ordinary view of the patient when assembled and cured. The shell member 22 and liner material 24 are generally clear or translucent, and may be fabricated to provide a sufficient texture or internal turbidity for suitable light-diffusing characteristics.

The silicone rubber and gel materials described above with reference to one embodiment of the shell member 22 and liner material 24 are particularly adapted for application to the external skin of the patient's body. It may be appreciated that the degree of inherent adhesion or tackiness exhibited by the liner material 24 may require adjustment or modification when the light-emitting treatment device 10 is intended to be applied to other regions of the patient's body, particularly to fragile wound tissue or internal tissues and organs. Other liner materials 24 having different adhesion values and peel strengths may be utilized, or a biocompatible non-adhesive material may be mixed with the liner material 24 to reduce its inherent quality, provided that curing can be performed and a unitary or integral bond to the shell member 22 may be formed if desired. In addition, referring particularly to FIG. 6, a predetermined or selected area 34 of the exposed skin-adhering surface of the liner material 24 may be coated or treated with a layer or agent which inhibits, diminishes, interferes with, or masks the skin-adhering quality of the liner material 24 in that area 34, leaving a peripheral zone 36 or pattern which maintains the normal skin-adhering quality of the liner material 24, while the area 34 will adhere less or not at all to the patient's body 14.

One or more light-emitting elements 18 in the form of optical fibers 20, VCSELs 28, LEDs, or other suitable therapeutic light sources may be incorporated in the light-emitting treatment device 10. Optical fibers 20 may be operatively connected via an optical fiber cable 38 or bundle, and coupled to a remote light source (not shown). The optical fibers 20 may be disposed in any suitable array which uniformly and efficiently disperses the light energy throughout the operative area of the light-emitting treatment device 10 covering the region of the patient's body 14 being treated. The pattern may include radiating spokes or a serpentine configurations as shown in FIGS. 1–2, or other variations and combinations thereof.

In fabricating one embodiment of the treatment device 10, the shell member 22 is first molded to form an area, recess, or cavity to receive the light-emitting elements 18, and the liner material 24 is then poured in a highly viscous liquid or syrup-like state into or onto the shell member 22 to at least partially or fully cover and encompass the light-emitting elements 18. The light-emitting elements 18 may be disposed in the shell member 22 prior to adding the liner material 24, or may be embedded in the liner material 24 after the liquid gel material has been poured into or onto the shell member 22 during the initial stages of the curing process. The liner material 24 is then allowed to cure or dry. The drying or curing process can occur at ambient temperatures, or may be assisted by the application of heat. In general, relatively little surface boundary distinction occurs between the light-emitting elements 18 and the liner material 24. Once cured or dried, the liner material 24 bonds securely with the shell member 22 and the light-emitting elements 18 to form a unitary or integral light-emitting treatment device 10.

The exposed surface 40 of the liner material 24 is generally highly tacky to skin and to the opposing surface 42 of the shell member 22. If the exposed surface 40 remains in contact with the opposing surface of the shell 22 for an extended period of time, for example, if the light-emitting treatment device 10 is wrapped circumferentially around an area being treated such as a finger or arm of the patient and adhered to itself, the liner material 24 will not permanently bond with the shell member 22. Thus, the liner material 24 will releasably adhere to the overlapped regions of the shell member 22 and the exposed surface 40 is not left behind on the shell member 22 when the two surfaces 20, 22 are intentionally peeled apart. The shell member 22 advantageously acts as a cohesive carrier of the liner material, and as an attachable but releasable anchoring substrate for the liner material 24. Due to the generally low shear or peel force properties of the liner material 24 when in contact with the "reverse" side of the shell member 22, the light-emitting treatment device 10 advantageously exhibits a self-limiting wrapping characteristic. The light-emitting treatment device 10 cannot be wrapped too tightly or it will naturally unpeel or unwrap itself, thereby preventing inadvertent constriction of blood circulation. The light-emitting treatment device 10 advantageously remains in place when properly sized for an area of treatment and correct tension is used on the patient's body 14. The light-emitting treatment device 10 advantageously conforms, and if necessary flexes and stretches slightly or substantially, to contact and cover a desired area for PDT. Stretching of the light-emitting treatment device 10 may intentionally be limited by controlling the elasticity of the shell member 22, embedding a limiting mesh or network of fibers, or by the circuitry, substrate, heat-dissipating structures, or coating layers used with or applied to the light-emitting treatment device 10. The light-emitting treatment device 10 self-adheres to the area contacted by the liner material 24, and may be used to uniformly distribute light energy within the region being treated. The treatment device 10 is generally easily removed from the skin or tissue of the patient's body 14 without discomfort or adverse affects on the skin or tissue. A hypodermic syringe may be used to inject a therapeutic pharmacological agent, marker, dye, or other substance through the light-emitting treatment device 10 without removing or lifting the light-emitting treatment device 10 away from the skin or tissue during treatment. Alternatively, a portion of the light-emitting treatment device 10 may be peeled away to expose the underlying skin or tissue, such as to apply other topical medications, or to clean or inspect the skin or tissue without removing or repositioning the remainder of the light-emitting treatment device 10.

Figure 5:
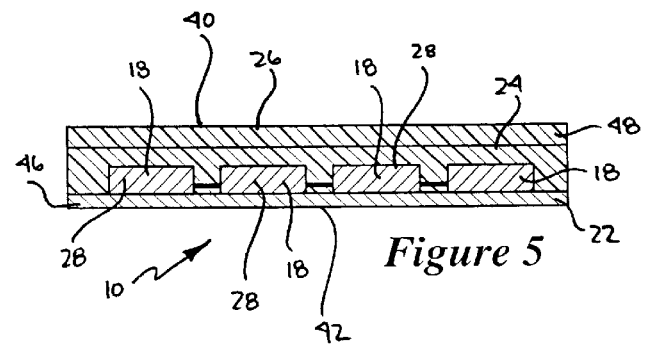
FIG. 5 is a cross-section view one embodiment of the light-emitting treatment device of FIG. 4 taken through line 5—5 of FIG. 4 showing an intermediate layer of VCSELs disposed between a heat dissipating layer and a light-diffusing layer.

FIG. 5 illustrates a cross-sectional view of an embodiment of a light-emitting treatment device 10 with an intermediate layer of VCSELs 28 disposed between a heat dissipating substrate 46 or layer and a light-diffusing layer 48. The light-diffusing layer 28 is preferably made of a silicone rubber or gel material compatible with the shell member 26 and liner material 24, and the heat-dissipating layer 46 is preferably made of a material configured to absorb or disperse heat generated by the VSCELs 28. The VCSELs 28 may be disposed in close proximity to one another, or spaced apart to facilitate flexing the substrate 48. One embodiment of the substrate 48 has dimensions on the order of 3.0 cm by 1.2 cm and includes arrayed tiles of VCSELs 28 having dimensions on the order of 0.3 cm by 0.3 cm.

The array of VCSELs 28 may be any size, shape, or wavelength suitable for a variety of treatment applications. The number of VCSELs 28 per array may be selectively determined, and will vary depending upon factors including the required light output (usually in milliwatts/cm$^2$). The VCSELs 28 are separated or spaced-apart from the tissue surface a predetermined distance that is dependent upon factors including the incident light energy necessary for treatment, beam divergence, and the thickness or opacity of the liner material 24 and any auxiliary light-diffusing layer 48. For example, given the above dimensions, the separation may be approximately 1–2 mm. The array may be sufficiently flexible or malleable to conform to a variety of body shapes or parts such as the tongue, palate, or cheek, as well as normally exposed skin areas having complex or irregular curvatures or tight curves, such as a patient's arm or leg, finger or toe, heel, wrist, or elbow.

Figure 7:
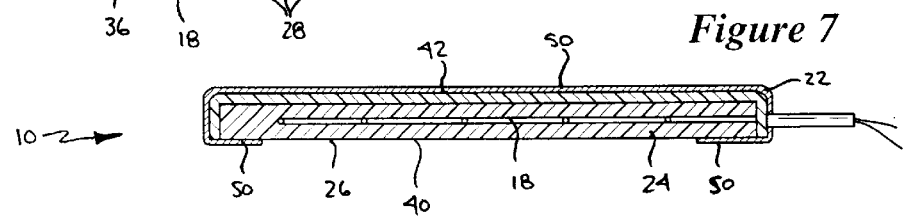
FIG. 7 is a cross-sectional view of an alternate embodiment of the light-emitting treatment device of the present invention showing a Light-blocking layer partially surrounding the shell member and liner material.
Figure 8:
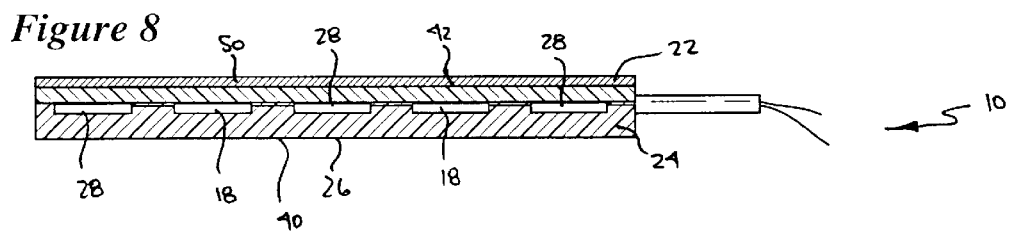
FIG. 8 is a cross-sectional view of another embodiment of the Light-emitting treatment device of the present invention showing the array of VSCELs disposed on the shell member and entirely covered by the liner material, with a light-blocking layer opposing the exposed surface of the liner material.

FIGS. 7 and 8 illustrate embodiments of the light-emitting treatment device 10 with a layer 50 of light-blocking material such as gold disposed on one or more surfaces to contain the transmitted light energy to a certain area. The light-blocking layer 50 may be fabricated on the light-emitting treatment device 10 in a predetermined pattern as dictated by certain prescribed PDT treatment techniques or protocols for specific conditions, or may be selectively added or applied at the time of treatment depending on the treatment region desired. The light-blocking layer 50 may cover any combination of the reverse side of the light-emitting treatment device 10 opposing the skin-adhering surface 40, the sides of the light-emitting treatment device 10, or portions of the tissue-confronting or skin-adhering surface 40 of the light-emitting treatment device 10.

FIG. 8 further illustrates an embodiment of the light-emitting treatment device 10 in which the shell member 22 does not define a recess or cavity, and the liner material 24 is formed around or substantially covering the light-emitting members 18 such as an array of VCSELs 28. The liner material 24 may be formed on the shell member 22 regardless of whether the shell member 22 defines a recess or cavity, and the liner material may partially surround or fully envelope the light-emitting elements 18 regardless of whether the light-emitting elements 18 are disposed within a recess or cavity defined by the shell member 22, or are positioned on a generally planar, convoluted, or irregularly-shaped shell member 22 forming a substrate, as well as spaced apart from the shell member 22 which forms the substrate.

Figure 6:
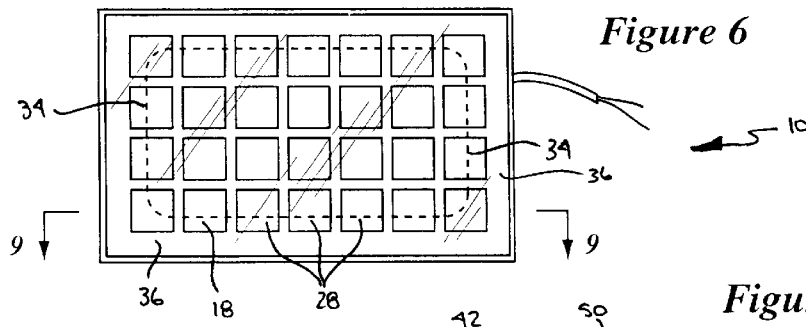
FIG. 6 is a plan view of an alternate embodiment of the light-emitting treatment device of the present invention having a tiled array of VCSELs as the light-emitting elements.
Figure 9:
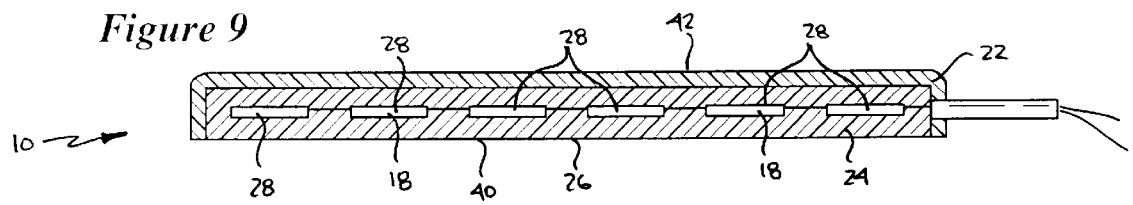
FIG. 9 is a cross-sectional view of the Light-emitting treatment device of FIG. 6 taken through line 9—9 in FIG. 6.

FIG. 9 is a side cross-section view of the light-emitting treatment device 10 of FIG. 6 showing a further embodiment in which the shell member 22 defines a recess receiving the liner material 18 and the light-emitting members 18 such as VCSELs 28, but the light-emitting members 18 are spaced apart from the shell member 22 or other substrate.

FIG. 10 illustrates the generally flexible patch-type embodiment of the light-emitting treatment device 10 of the present invention disposed on the skin surface of the patient's body 14, such as the back of the patient's left hand, and connected via a cable 32 to a control unit and power supply 30.

FIG. 11 illustrates a shaped-article embodiment of the light-emitting treatment device 10 that is shaped in the form of a particular part of the patient's body 14, and is therefore sufficiently rigid or inflexible so as to hold its predetermined shape or return to its predetermined shape if deformed, but malleable or pliable enough to permit it to be deformed as necessary to apply or attach it to the patient's body 14. The representative example of the shaped-article embodiment of the light-emitting treatment device 10 is a dental mouthpiece 52 including light-emitting elements 18 such as VCSELs 28 which may applied over the patient's teeth, gums, or palate. The shaped-article embodiment of the light-emitting treatment device 10 may similarly be formed of a silicone rubber shell member 22 and silicone gel liner material 24 that will conform and adhere to the surface area to be treated using PDT. The shaped-article embodiment of the light-emitting treatment device 10 may utilize light-emitting elements 18 in the form of optical fibers 20, VCSELs 28, LEDs, or other light sources, and it similarly operatively coupled to a remotely-located control unit and power supply 30 using a optical fiber cable 38 or suitable electrical wire or cable 32.

It is expected that the light-emitting treatment device 10 in the form of a flexible pad 12, a shaped-article, or another selected configuration will be provided to the medical professional in a sterile packaged form, removed from its packaging in preparation for a PDT procedure, and coupled prior to treatment to the control unit and power supply 30 using a suitable connector 54 or coupler.

The above-described embodiments of the present invention, including the light-emitting treatment device 10 and the method for making the light-emitting treatment device 10, are merely descriptive of its structural, functional, and operating principles and are not to be considered limiting. Further modifications to or adaptations of the invention herein disclosed will occur to those skilled in the respective art, and all such modifications or adaptations are deemed to be within the scope of the invention as recited by the following claims.

What is claimed is:

1. A light-emitting treatment device for irradiating a region of a patient's body to be treated using one or more light-emitting elements which emit a light, the light-emitting treatment device comprising:

a support member fabricated from a flexible pad of a material which at least partially encapsulates the one or more light-emitting elements and intrinsically defines a tissue-adhering surface having an inherently tacky characteristic, the one or more light-emitting elements being disposed on the flexible pad and configured to irradiate the region of the patient's body with a portion of the material forming the flexible pad being interposed between the one or more light-emitting elements and the tissue-adhering surface such that the light is transmitted through the portion of the material disposed between the one or more light-emitting members and the tissue-adhering surface, so that the tissue-adhering surface of the support member is placed in contact with the patient's body proximate to or covering the region to be irradiated, and the support member conforms and adheres to the patient's body such that the one or more light-emitting elements irradiate the region of the patient's body to be treated.

2. The light-emitting treatment device of claim 1 wherein the support member comprises:
   a shell member defining an area for receiving the one or more light-emitting elements; and
   a liner material disposed on or within the shell member and at least partially encompassing the one or more light-emitting elements, the liner material defining the tissue-adhering surface for contacting the patient's body proximate to the region being irradiated.

3. The light-emitting treatment device of claim 2 wherein the shell member is fabricated from a molded silicone rubber.

4. The light-emitting treatment device of claim 2 wherein the liner material is fabricated from a curable silicone gel.

5. The light-emitting treatment device of claim 2 wherein the shell member defines a cavity receiving the one or more light-emitting elements, and the liner material is a cured gel disposed within the cavity at least partially encompassing the one or more light-emitting elements.

6. The light-emitting treatment device of claim 5 wherein the shell member and the liner material have flexibility characteristics comparable to one another, such that the shell member and the liner material may be flexed or stretched sufficiently for application to an irregularly-shaped portion of the patient's body without separating from one another.

7. The light-emitting treatment device of claim 5 wherein the shell member and the liner material form a substantially unitary and integral assembly.

8. The light-emitting treatment device of claim 1 wherein the support member is a substantially flexible pad which conforms to the portion of the patient's body to which the flexible pad is adhered.

9. The light-emitting treatment device of claim 1 wherein the tissue-adhering surface of the support member may be peeled off the patient's body, washed, and subsequently repositioned on the patient's body while the tissue-adhering surface maintains the inherently tacky characteristic.

10. The light-emitting treatment device of claim 1 wherein the tissue-adhering surface of the support member will responsively peel off the patient's body when sufficient lateral force is applied to the support member by stretching the support member across the portion of the patient's body above a predetermined threshold for normal use in photodynamic therapy.

11. The light-emitting treatment device of claim 1 wherein a portion of the liner material which defines the tissue-adhering surface covers the light-emitting elements and is disposed between the light-emitting elements and the region of patient's body being treated.

12. The light-emitting treatment device of claim 1 wherein the one or more light-emitting elements are entirely embedded within the material.

13. The light-emitting treatment device of claim 1 wherein the material interposed between the one or more light-emitting elements and the tissue-adhering surface diffuses the light as the light is transmitted through the material.

14. A method for fabricating a light-emitting treatment device utilizing one or more light-emitting elements for irradiating a region of a patient's body, the method comprising the steps of:

providing a substrate member;

positioning the one or more light-emitting elements on an area of the substrate member;

disposing a covering material in an uncured state onto the substrate member so that the covering material at least partially encompass the one or more light-emitting elements, the covering material defining a tissue-adhering surface which has an inherently tacky characteristic, the tissue-adhering surface being generally exposed; and curing the covering material such that the tissue-adhering surface remains exposed and retains the inherently tacky characteristic, so that in use the tissue-adhering surface of the covering material may be placed in contact with and adhere to the patient's body proximate to or in overlying relation to the region to be irradiated, and the substrate member and covering material will conform to the patient's body such that the one or more light-emitting elements irradiate the region of the patient's body to be treated.

15. The method of claim 14 wherein the step of providing the substrate member further comprises the step of:
   injection molding the substrate member using a silicone rubber material.

16. The method of claim 14 wherein the substrate member defines a cavity receiving the one or more light-emitting elements and the step of disposing the covering material onto the substrate member further comprises the step of:
   pouring the covering material in the uncured state as a viscous liquid into the cavity defined by the substrate member so as to at least partially cover the light-emitting elements.

17. The method of claim 16 wherein the covering material is a silicone gel material.

18. The method of claim 14 wherein the light-emitting treatment device is applied to an irregularly-shaped portion of a patient's body, and further wherein the substrate member and the covering material form a substantially unitary and integral assembly upon the curing of the covering material, such that the substrate member and the covering material may be flexed or stretched sufficiently for application to the irregularly-shaped portion of the patient's body without separating from one another.

19. A method for fabricating a light-emitting treatment device utilizing one or more light-emitting members for irradiating a region of a patient's body with light, the method comprising the steps of:
   embedding the one or more light-emitting elements in a material forming a tissue-contacting surface; and
   curing the material, such that when the material is cured the tissue-contacting surface intrinsically has an inherently tacky characteristic, so that in use the tissue-contacting surface may be placed in contact with and adhere to the patient's body proximate to or covering the region to be irradiated, and the light-emitting treatment device will conform to the patient's body such that the one or more light-emitting elements irradiate the region of the patient's body to be treated.

20. The method of claim 19 wherein the step of embedding the one or more light-emitting members in the material includes disposing a portion of the material between the one or more light-emitting members and the tissue-contacting surface, such that the light is transmitted through the portion of the material disposed between the one or more light-emitting members and the tissue-contacting surface.

* * * * *